United States Patent
Zhao

(10) Patent No.: US 12,164,071 B2
(45) Date of Patent: Dec. 10, 2024

(54) METHOD AND APPARATUS FOR IDENTIFYING LOCATION SPECTRUM, AND COMPUTER STORAGE MEDIUM

(71) Applicant: RAYCAN Technology Co., Ltd. (Suzhou), Jiangsu (CN)

(72) Inventor: Anjiang Zhao, Jiangsu (CN)

(73) Assignee: RAYCAN Technology Co., Ltd. (Suzhou) (CN)

( * ) Notice: Subject to any disclaimer, the term of this patent is extended or adjusted under 35 U.S.C. 154(b) by 395 days.

(21) Appl. No.: 17/597,642

(22) PCT Filed: Jul. 2, 2020

(86) PCT No.: PCT/CN2020/099959
§ 371 (c)(1),
(2) Date: Jan. 14, 2022

(87) PCT Pub. No.: WO2021/031711
PCT Pub. Date: Feb. 25, 2021

(65) Prior Publication Data
US 2022/0163686 A1   May 26, 2022

(30) Foreign Application Priority Data

Aug. 19, 2019   (CN) .......................... 201910764960.8

(51) Int. Cl.
*G01T 1/29* (2006.01)
*A61B 6/03* (2006.01)
*G01T 1/202* (2006.01)

(52) U.S. Cl.
CPC ............ *G01T 1/2985* (2013.01); *G01T 1/202* (2013.01); *A61B 6/037* (2013.01)

(58) Field of Classification Search
None
See application file for complete search history.

(56) References Cited

U.S. PATENT DOCUMENTS

| | | | | |
|---|---|---|---|---|
| 6,169,285 B1 * | 1/2001 | Petrillo | ................. | G01T 1/1647 250/369 |
| 8,452,064 B2 * | 5/2013 | Ross | .................... | G06T 11/005 382/131 |

(Continued)

FOREIGN PATENT DOCUMENTS

| | | |
|---|---|---|
| CN | 101996325 A | 3/2011 |
| CN | 103177252 A | 6/2013 |

(Continued)

OTHER PUBLICATIONS

Machine Translation.*

(Continued)

*Primary Examiner* — David P Porta
*Assistant Examiner* — Djura Malevic
(74) *Attorney, Agent, or Firm* — KLEMCHUK PLLC

(57) ABSTRACT

A method, device, and computer storage medium for identifying position spectrum. The method comprises: pre-processing an initial position spectrum to generate a first position spectrum; extracting feature from the first position spectrum to generate a plurality of second position spectra; performing a peak search on the second position spectra to obtain N peak points, which furan a third position spectrum; globally numbering the peak points in the third position spectrum to form a sixth position spectrum; and clustering single events based on the peak points in the sixth position spectrum to form a final position spectrum. The device comprises a pre-processing unit, a feature extraction unit, a peak search unit, a global numbering unit and an event clustering unit. The above method may be realized when executing programs in a computer storage medium.

17 Claims, 9 Drawing Sheets

(56) References Cited

U.S. PATENT DOCUMENTS

| | | | |
|---|---|---|---|
| 9,316,743 B2* | 4/2016 | Rousso | G01T 1/1647 |
| 10,149,657 B2* | 12/2018 | Xie | G01T 1/1647 |
| 11,531,125 B2* | 12/2022 | Xu | G06T 15/00 |
| 11,644,586 B2* | 5/2023 | Chen | A61B 6/02 |
| | | | 250/252.1 |
| 2005/0145797 A1* | 7/2005 | Oaknin | A61B 6/037 |
| | | | 250/363.04 |
| 2008/0128626 A1* | 6/2008 | Rousso | A61B 6/4258 |
| | | | 250/362 |
| 2008/0230702 A1* | 9/2008 | Rousso | A61B 6/4258 |
| | | | 250/363.02 |
| 2011/0135179 A1* | 6/2011 | Ross | A61B 6/583 |
| | | | 382/131 |
| 2014/0270443 A1* | 9/2014 | Vija | A61B 6/5258 |
| | | | 382/131 |
| 2016/0321808 A1* | 11/2016 | Zhou | G06T 11/005 |
| 2016/0324498 A1* | 11/2016 | Xie | A61B 6/037 |
| 2022/0163686 A1* | 5/2022 | Zhao | G06T 7/73 |

FOREIGN PATENT DOCUMENTS

| | | | |
|---|---|---|---|
| CN | 101996325 B * | 9/2013 | |
| CN | 103914860 A | 7/2014 | |
| CN | 2015010393 A1 | 1/2015 | |
| CN | 104337531 A | 2/2015 | |
| CN | 104732541 A | 6/2015 | |
| CN | 106295639 A | 1/2017 | |
| CN | 106526651 A | 3/2017 | |
| CN | 107238854 A | 10/2017 | |
| CN | 107979987 A | 5/2018 | |
| CN | 104732541 B * | 7/2018 | |
| CN | 110471102 A | 11/2019 | |

OTHER PUBLICATIONS

Chen, Xin et al., Fast Online Crystal Identification Algorithm in Positron Emission Tomography, China Sciencepaper, Apr. 30, 2013, vol. 8, No. 4 (ISSN:2095-2783).

Foreign communication from the priority International Application No. PCT/CN2020/099959 PCT, International Search Report, 5 pages.

Foreign communication from the priority Internation Application No. PCT/CN2020/099959 PCT, Written Opinion of the International Searching Authority, 5 pages.

Foreign Communication for Application No. 201910764960.8 dated Aug. 19, 2019, First Office Action dated Sep. 3, 2020, 13 pages.

Foreign Communication for Application No. 201910764960.8 dated Aug. 19, 2019, Second Office Action dated Mar. 25, 2021, 7 pages.

* cited by examiner

METHOD AND APPARATUS FOR IDENTIFYING LOCATION SPECTRUM, AND COMPUTER STORAGE MEDIUM

CROSS-REFERENCE TO RELATED APPLICATIONS

This application is a filing under 35 U.S.C. 371 of International Application No. PCT/CN2020/099959, filed Jul. 2, 2020, entitled "Method and Apparatus for Identifying Location Spectrum, and Computer Storage Medium," which claims priority to Chinese Patent Application No, 201910764960.8 filed Aug. 19, 2019, which applications are incorporated by reference herein in their entirety.

TECHNICAL FIELD

The disclosure is related to a field of image processing, and more particularly to a method, device, and computer storage medium for identifying position spectrum.

BACKGROUND

Positron Emission Tomography (abbr. PET) is a non-invasive imaging method. The principle of PET is to label a radionuclide capable of generating positrons on a molecular probe and inject it into the organism. The positrons generated by the decay of the radionuclide collide with the negative electrons in the organism and annihilate, and at the same time release a pair of gamma photons with energy of 511 keV and moving in the opposite directions, A position-sensitive radiation detector arranged around the organism is provided for converting the received gamma photons into electrical signals so as to obtain the energy, position, and time information of the annihilation event. By means of the annihilation coincidence technology, furthermore, the position of the response line where the annihilation event is located is obtained, and by means of the two-dimensional or three-dimensional tomographic reconstruction algorithm, the distribution of radionuclides inside the organism is also obtained, so as to observe the physiological and biochemical changes in the organism in vitro.

PET imaging equipment can obtain the position information of the annihilation event through the radiation detector at the front end. The radiation detector usually adopts a structure in which a crystal array and a photoelectric conversion device, such as a photomultiplier tube or a silicon photomultiplier tube, are coupled to each other, that is, the crystal, also known as scintillation crystal, are cut into crystal bars of a certain specification, and then several crystal bars are arranged according to a certain order to form a crystal array, also known as a module, and then the crystal array is coupled to the photoelectric conversion device to form a radiation detector. When performing radiation detection, a large number of gamma photons fly in different angles. When gamma photons are incident on a crystal bar in the crystal array, the crystal bar interacts with the gamma photons to generate fluorescence, which is then transferred to the optoelectronics and is converted into a corresponding electrical signal output by the photomultiplier device, Using the electrical signals, the coordinates (x, y) of the incident position of the gamma photons can be calculated, and the coordinate system XOY can be established according to the cross section of the crystal array, Finally, according to the position coordinate information, it may determine from which crystal bar the gamma photons are incident.

Ideally, the corresponding relationship between the position coordinates and the crystal bar is a linear relationship, that is to say, when the dynamic change range of the position coordinates (x, y) is divided in proportion to the size of the crystal bar, each range linearly corresponds to a coordinate zone covered by the cross-section of one crystal bar. However, in practical applications, due to the nonlinearity of the spatial response of the radiation detector, the inconsistent specifications of crystal strips, certain differences in physical characteristics, and Compton scattering, the linear correspondence relationship may always present nonlinear features. In order to ensure the accuracy of the corresponding relationship, it is needed to establish a position spectrum, and define an accurate corresponding relationship between the crystal bar and the position coordinates (x, y) in the position spectrum. In order to meet the high position resolution requirements of PET imaging equipment, this correspondence needs to be very accurate. Therefore, how to establish a reasonable and correct position spectrum has become the focus of attention in this field.

When establishing a position spectrum, a two-dimensional position scatter plot, or a two-dimensional position histogram, may usually be used, which records the number of incident gamma photons measured at each coordinate position, There are several existing methods for establishing position spectrum, which are all based on scatter plots of experimental measurements. Their general idea is to first determine the boundary of each crystal bar, and then use the boundary information to establish the position spectrum. Rogers et al. used the centroid of each small zone as the peak point of the area, and then found out the local minimum points at the periphery, and used the local minimum points as the boundaries of the corresponding crystal bar. The advantage of the method is that there is no dead zone of detection in the crystal bar, each of the position coordinates corresponding to a crystal bar, without discarded scintillation event, such that the sensitivity of the detection system will not be degraded. The method is relatively intuitive and easy to understand, but lacks a rigorous theoretical basis, Stronger and Johnson et al., according to the Gaussian mixture model (GMM) as the theoretical basis, gave a method for establishing a position spectrum for a crystal array. This method improves the accuracy of the established position spectrum, but there still exists need for improvement in specific implementation. For example, multiple use of the mean value deletion method during the local peak search, is likely to cause mistaken deletion. Meanwhile, during the local peak search, the number of crystal bars is set as the loop termination condition, while the local peak points as found may be false local peak points, such that the true local peak points may be missed. In the prior art, semi-automatic or automatic position spectrum segmentation methods may also be used, such as using a watershed algorithm to obtain peak points of crystal positions, finding unidentified position points by straight line fitting, and then segmenting the position spectrum. However, the methods also involve the problems that the edges of the position spectrum are blurred, and the deformation is serious which leads to difficulty in accurate identification.

In general, the method for realizing position spectrum segmentation in the prior art lacks applicability, with a poor identification effect of position spectrum with blurry edges and severe deformation, and low accuracy. Meanwhile, in the prior art can only the position spectrum with certain features be effectively identified, which leads to the incapability of addressing the issues that the position spectra generated by different radiation detectors may contain various features and represent great differences from each other.

SUMMARY

The purpose of the present invention is to provide a method, a device, and a computer storage medium for identifying a position spectrum, so as to solve at least one of the above-mentioned problems in the prior art.

To solve the above-mentioned technical problem, it is proposed in the disclosure to provide a method for identifying a position spectrum, the position spectrum being a two-dimensional position distribution image of photons, and containing position information of all photons extracted from single events output from a detector, wherein the method comprises the following steps:

step S1: pre-processing an initial position spectrum to generate a first position spectrum;

step S2: extracting features from the first position spectrum to generate a plurality of second position spectra;

step S3: performing a peak search on the second position spectra to obtain N peak points, which form a third position spectrum, wherein N is the number of scintillation crystals in the detector;

step S4: globally numbering the peak points in the third position spectrum to form a sixth position spectrum; and step S5: clustering the single events based on the peak points in the sixth position spectrum to form a final position spectrum, so as to realize the position spectrum segmentation.

In an embodiment in the disclosure, in the step S1, the pre-processing comprises specific steps of: selecting a size and a first variance of a first Gaussian template, and processing the initial position spectrum by means of convolution with the first Gaussian template to generate the first position spectrum.

In an embodiment in the disclosure, in the step S1, the feature extraction comprises specific steps of:

step S21: determining a set of second variances $\sigma_1, \sigma_2, \ldots, \sigma_n \sigma_n$, where n is a natural number, and generating n Gaussian templates according to each of the second variances with the same size, denoted as g;

step S22: finding Hessian matrices $$H(L) = \begin{bmatrix} L_{xx} & L_{xy} \\ L_{xy} & L_{yy} \end{bmatrix}$$

by a convolution of each second Gaussian template and the first position spectrum, wherein, x and y represent the corresponding orthogonal coordinate axes in the image of the position spectrum;

step S23: calculating determinants of the n Hessian matrices, that is $D=L_{xx} \times L_{yy} - L_{xy}^2$, and generating n second position spectra.

In an embodiment in the disclosure, in the step S22, finding the Hessian matrices comprises specific steps of:

first, calculating a second-order partial derivative of the second Gaussian template with respect to x according to the various second variances;

$$\frac{\partial^2 g}{\partial x^2} = \frac{1}{2\pi\sigma^4} e^{-\frac{x^2+y^2}{2\sigma^2}} \left( \frac{x^2}{\sigma^2} - 1 \right);$$

second, calculating a second-order partial derivative of the second Gaussian template with respect to y according to the various second variances:

$$\frac{\partial^2 g}{\partial y^2} = \frac{1}{2\pi\sigma^4} e^{-\frac{x^2+y^2}{2\sigma^2}} \left( \frac{y^2}{\sigma^2} - 1 \right);$$

third, calculating a partial derivative with respect to y based on a partial derivative of the second Gaussian template with respect to x according to different second variances:

$$\frac{\partial^2 g}{\partial x \partial y} = \frac{1}{2\pi\sigma^4} e^{-\frac{x^2+y^2}{2\sigma^2}} \left( \frac{xy}{\sigma^2} \right);$$

fourth, normalizing the said three partial derivatives, that is, multiplying $\sigma^2$, and then convolving the three partial derivatives with the first position spectrum respectively to obtain n $L_{xx}$, $L_{xy}$, $L_{yy}$, such that n Hessian matrices are obtained, where g is the second Gaussian template, and x and y are orthogonal coordinate axes corresponding to the cross section of the scintillation crystals in the detector.

In an embodiment the disclosure, in the step S3, before performing the peak search, the second position spectra are morphologically expanded to generate expanded position spectra.

In an embodiment in the disclosure, in the step S3, the peak search comprises the step of searching for N maximum values among the expanded position spectra, so as to form the third position spectrum.

In an embodiment in the disclosure, in the step S4, the globally numbering comprises specific steps of:

step S41: obtaining the position coordinates and position response radii of all the peak points;

step S42: extracting the zones where the position coordinates of the peak points are located within the position response radii;

step S43: calculating the minimum values of a correspondingly dimensional coordinate in each of the zones in the row or column direction;

step S44: ranking the N minimum values, such that the peak points corresponding to the $m \times (n-1)+1^{th}$ to $m \times n^{th}$ minimum values belong to the $n^{th}$ row/column, where m is the number of scintillation crystals in a row/column, n is a natural number; and step S45: numbering the rows or columns assigned according to the peak points in the actual geometric order of the scintillation crystal array, and displaying the numbers adjacent to the peak points to form a sixth position spectrum.

In an embodiment in the disclosure, in the step S5, event clustering comprises after obtaining the position coordinates of the peak points in the position spectrum, clustering all the single events according to the position information to generate a crystal lookup table and to obtain the segmentation result of the position spectrum.

In an embodiment in the disclosure, the event clustering comprises specific steps of:

step S51: randomly selecting position coordinate of a single event, and calculating distances between the position coordinate and position coordinates of the N identified peak points;

step S52: selecting the peak point with the shortest distance among the N distances in the step S51 as the crystal cluster of the position coordinates in the step S51; and step S53: traversing the position coordinates of all the single events to obtain crystal clusters for all the position coordinates, and distinguishing different classes from each other to form the final position spectrum.

In an embodiment in the disclosure, the method may further include the following steps:

step S31: removing invalid peak points in the third position spectrum to form a fourth position spectrum;

step S32: assigning rows or columns of all the peak points after the removal to form a fifth position spectrum;

step S33: predicting missing peak points in the fifth position spectrum.

In an embodiment in the disclosure, in the step S31, removing invalid peak points includes the specific steps of:

step S311: extracting the image of position distribution zones for all the peak points according to the position coordinates of the peak points and the second variances;

step S312: determining an initial segmentation threshold T, recording the ratio of the number of pixels smaller than a initial segmentation threshold T in the image of the position distribution zones to the number of all pixels as w0, and the average gray as u0; and recording the ratio of the number of pixels greater than the initial segmentation threshold T in the image of the position distribution zones to the number of all pixels as w1, and the average gray level as u1;

step S313: calculating the inter-Class variance k according to the formula $k = w_0 \times w_1 \times (u_0 - u_1)^2$;

step S314: traversing the values of the initial segmentation threshold T to maximize the inter-class variance k, thereby obtaining a binarized image of the position distribution zones of the scintillation crystals;

step S315: obtaining a neighborhood in the center of the binarized image and calculating a pixel sum, wherein if the value of the pixel sum in the neighborhood is 0, the peak point is determined to be an invalid peak point.

In an embodiment in the disclosure, in the step S32, the assignment of rows or columns comprises specific steps of;

step S321: ranking the position coordinates of the peak points identified in the step S31 according to the corresponding dimensional coordinate;

step S322: extracting the $m \times (n-1)+1^{th}$ to $m \times n^{th}$ peak points as a fuzzy row set of the $n^{th}$ row or column, where m is the number of crystals on each row, and n is a Natural number;

step S323: randomly selecting p peak points from the fuzzy row set of the $n^{th}$ row or column as the point set S participating in the fitting, with a set of the remaining peak points in the set of remaining extreme points as a remainder set R, where p is the number of samples required for fitting a curve;

step S324: performing quadratic-curve fitting on the extreme points in the point set S;

step S325: obtaining an error sum E for all the peak points in the remainder set R with respect to the quadratic curve;

step S326: iteratively performing step S323 to step S325 until within a certain number of iterations, the minimum value of the error sum E or the error sum E is less than a defined minimum tolerance threshold, to obtain the distribution curve of peak points in the $n^{th}$ row or column; and step S327: assigning the identified peak points to the distribution curve of each row/column according to the principle of the assignment of rows or columns.

In an embodiment in the disclosure, the principle of assignment of rows or columns includes near assignment principle and conflict assignment principle.

In an embodiment in the disclosure, the principle of near assignment may include the assignment based on the nearest distance between the peak point and the intersection of the distribution curve; each intersection of the distribution curve occupying at most one peak point, and one peak point being assigned only one intersection.

In an embodiment in the disclosure, the conflict assignment principle comprises: finding the corresponding peak points by the intersection of the distribution curve; finding two nearest intersections for each of the corresponding peak points; and comparing the sum of distances between each peak point and the two nearest intersections with each other, the peak point with the greatest sum of distances being assigned to the conflict intersection of the distribution curves.

In an embodiment in the disclosure, in the step S33, predicting the missing points comprises specific steps of: finding out the coordinates of the intersection unassigned with peak points, and assigning the coordinates of the intersection to the missing peak points in the current row and the current column.

In the disclosure, a device for identifying a position spectrum is provided, comprising: a pre-processing unit, a feature extraction unit, a peak search unit, a global numbering unit, and an event clustering unit. The pre-processing unit is configured to receive an initial position spectrum output from a detector and pre-process the initial position spectrum to firm a first position spectrum. The feature extraction unit is configured to receive the first position spectrum and extract features from the first position spectrum to generate second position spectra. The peak search unit is configured to receive the second position spectra and perform a peak search on the second position spectra to firm a third position spectrum. The event clustering unit is configured to cluster single events based on the peak points in the sixth position spectrum to form a final position spectrum, so as to realize the segmentation of the position spectrum.

According to an embodiment in the disclosure, the device may further comprises: an invalid value removal unit, a row and column assignment unit, and a missing point prediction unit, The invalid value removal unit is configured to remove invalid peak points in the third position spectrum to form a fourth position spectrum. The row and column assignment unit is configured to assign rows or columns of the peak points in the fourth position spectrum to form a fifth position spectrum; and The missing point prediction unit is configured to predict missing peak points in the fifth position spectrum.

In the disclosure, a computer storage medium is also provided which stores a computer program, wherein when the computer program is executed by a processor, the method in the above-mentioned embodiments may be realized.

By means of the method, the device, and the computer storage medium for segmenting a position spectrum, any position spectrum may be fully automatically processed as needed, or the position spectrum may be segmented before being processed as needed, with the capacity of high efficient and high accurate identification of the position spectrum with fuzzy edges and severe deformation, and it is possible to realize the effective identification of the position spectrum generated by various structural detectors.

BRIEF DESCRIPTION OF THE DRAWINGS

The accompanying drawings with reference to the embodiments or state of art will be described for the purpose of demonstrating the embodiments of the invention and the state of art. It is apparent that the figures as shown are merely illustrative of some embodiments as recited in the disclosure. It should be understood by those skilled in the art that various alternatives to the figures as shown may be appreciated, without creative work involved.

DETAILED DESCRIPTION

In the following, the invention will be described further with reference to embodiments. It should be understood that the following embodiments are for illustrative instead of limitative purpose only.

Notably, when a component or element is referred to as being "disposed on" another component or element, it can be directly disposed on the other component or element or there may be an intermediate component or element. When a component or element is referred to as being "connected or coupled" to another component or element, it may be directly connected or coupled to the other component or element or there is an intermediate component or element. The term "connection or coupling" used herein may include electrical connection or coupling and/or mechanical or physical connection or coupling. The term "comprise or include" used herein refers to the existence of features, steps, components or elements, but does not exclude the existence or addition of one or more further features, steps, components, or elements. The term "and/or" used herein includes any or all combinations of one or more of the related listed items.

Unless otherwise indicated, all the technical and scientific terms used herein have the general meaning as commonly understood by those skilled in the technical field related to the disclosure. The terms used herein are for the purpose of describing specific embodiments, but not intended to limit the invention.

In addition, the terms "first", "second", "third" or the like used herein are only for the purpose of description and to distinguish similar objects from each other, which do not express the sequence thereof, nor can they be understood as an indication or implication of relative importance. In addition, in the description of this disclosure, unless otherwise specified, "a plurality of" means two or more.

Figure 1:
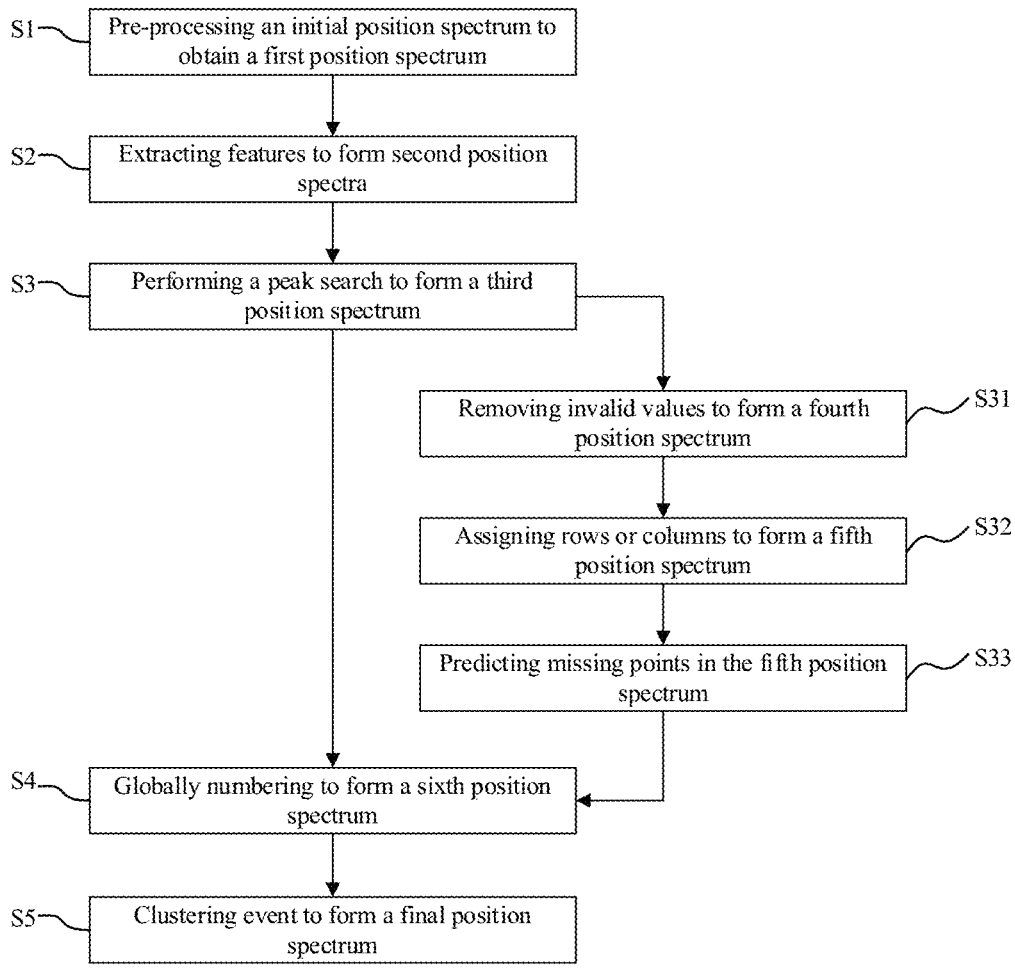
FIG. 1 shows a schematic view of the steps of a method for identifying a position spectrum according to an embodiment of the invention.

As shown in FIG. 1, the method for identifying a position spectrum provided in the disclosure may include the following steps:
   step S1: pre-processing an initial position spectrum to generate a first position spectrum;
   step S2: extracting features from the first position spectrum to generate a plurality of second position spectra;
   step S3: performing a peak search on the second position spectra to obtain N peak points, which form a third position spectrum, wherein N is the number of scintillation crystals in a detector;
   step S4: globally numbering the peak points in the third position spectrum to form a sixth position spectrum; and
   step S5: clustering single events based on the peak points in the sixth position spectrum to form a final position spectrum, so as to realize the segmentation of the position spectrum.

More specifically, before the above-mentioned step S1, the initial position spectrum may be obtained by apparatus or method commonly used in the art by the person skilled in the art. For example, the initial position spectrum may be obtained by a SiPM detector and by means of a multi-threshold sampling method, or by a PSPMT detector and by means of the multi-threshold sampling method. That is, the initial position spectrum in the application may be the spectrum obtainable by any method and apparatus in the state of art. It is known to the person skilled in the art that the position spectrum may be a two-dimensional position distribution image of all photons generated by the position information extracted from the single event data output by the PET detector, each pixel value in the image representing the number of the deposited photons in the two-dimensional coordinate, the light spots in the image indicating the position distribution of the photons generated by the various crystal bars, and the greater pixel value representing the greater number of the photons that fall into the position. The initial position spectrum in the application may be a position spectrum with sharp edges and little distortion, or a position spectrum with fuzzy edges and severe distortion. In the state of art, the sharpness of the edge and the magnitude of the distortion in the position spectrum may be evaluated according to the experience of those skilled in the art, which involves no difficulty in the state of art and will not be elaborated herein.

Figure 2:
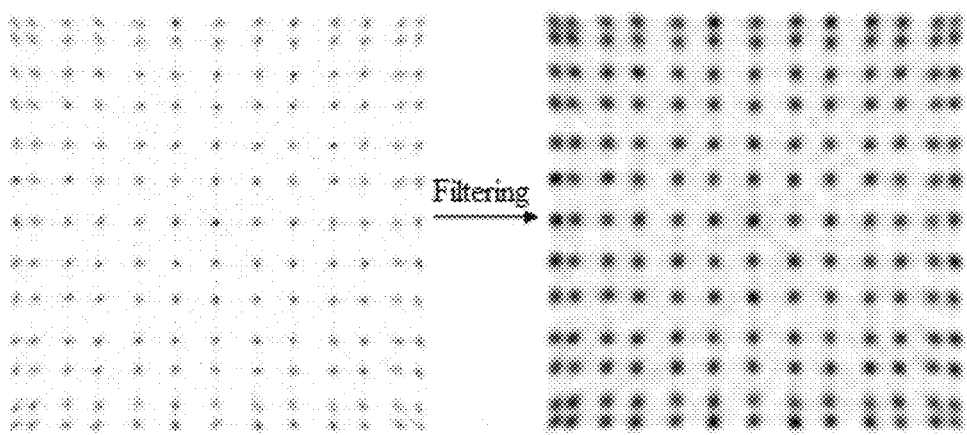
FIG. 2 shows a schematic view of the effect of the method for identifying position spectra according to an embodiment of the invention, in which the initial position spectrum (left) is obtained by a SiPM (silicon photomultiplier) detector, and the first position spectrum (right) can be obtained by means of filtering process of the initial position spectrum.

In the above-mentioned step S1, the specific method for pre-processing the initial position spectrum may involve using two-dimensional Gaussian filtering. Specifically, a size and a first variance of the first Gaussian template may be selected randomly or according to actual experience of the person skilled in the art. And then the initial position spectrum may be processed by means of convolution with the first Gaussian template to generate the first position spectrum. The selection of the first Gaussian template, the size and the first variance of the first Gaussian template, and the convolution operation are conventional to the person skilled in the art, which involves no difficulty in the state of art and will not be elaborated herein. By means of pre-processing, each light spot in the initial position spectrum may become more uniform and obvious. That is, the shape and distribution of the light spots in the initial position spectrum become closer to a two-dimensional Gaussian function, as shown in FIG. 2.

In the above-mentioned step S2, considering the first position spectrum's key feature lies in the local light spot, it is needed to perform feature extraction on the light spot in the first position spectrum for the capacity of correctly identifying the light spot in a wider range. Therefore, the similarity between the light spots and a differential operator is evaluated in terms of the distribution features of the light spots by means of a derivative-based differential method. The distribution features of the light spots refer to the distribution of the light spots on the two-dimensional coordinate, such as the arrangement and shape of the light spots, which may include high middle counts in the middle and low counts in the periphery, that is, the middle of the light spot is clear and the periphery is blurred. The extracting feature may comprise specific steps of:
   step S21: determining a set of second variances $\sigma_1$, $\sigma_2$, ..., $\sigma_n \sigma_n$, where n is a natural number, and $\sigma_n$ generating a two-dimensional Gaussian template according to each second variance with the same size, that is, generating n second Gaussian templates, denoted as g, and at the same time establishing an orthogonal coordinate system XOY corresponding to the image of the position spectrum based on the cross-section of the scintillation crystals in the detector device;
   Step S22: finding a solution of a convolution of each second Gaussian template and the first position spectrum, that is, finding the Hessian matrices:
   first, calculating a second-order partial derivative of the second Gaussian template with respect to x according to the various second variances:

$$\frac{\partial^2 g}{\partial x^2} = \frac{1}{2\pi\sigma^4} e^{-\frac{x^2+y^2}{2\sigma^2}} \left(\frac{x^2}{\sigma^2} - 1\right);$$

second, calculating a second-order partial derivative of the second Gaussian template with respect to y according to the various second variances:

$$\frac{\partial^2 g}{\partial y^2} = \frac{1}{2\pi\sigma^4} e^{-\frac{x^2+y^2}{2\sigma^2}} \left(\frac{y^2}{\sigma^2} - 1\right);$$

third, calculating a partial derivative with respect to y based on a partial derivative of the second Gaussian template with respect to x according to different second variances:

$$\frac{\partial^2 g}{\partial x \partial y} = \frac{1}{2\pi\sigma^4} e^{-\frac{x^2+y^2}{2\sigma^2}} \left(\frac{xy}{\sigma^2}\right);$$

finally, normalizing the said three partial derivatives, that is, multiplying $\sigma^2$, and then convolving the three partial derivatives with the first position spectrum respectively to obtain n $L_{xx}$, $L_{xy}$, $L_{yy}$, such that n Hessian matrices may be obtained, namely $$H(L) = \begin{bmatrix} L_{xx} & L_{xy} \\ L_{xy} & L_{yy} \end{bmatrix};$$

Figure 3:
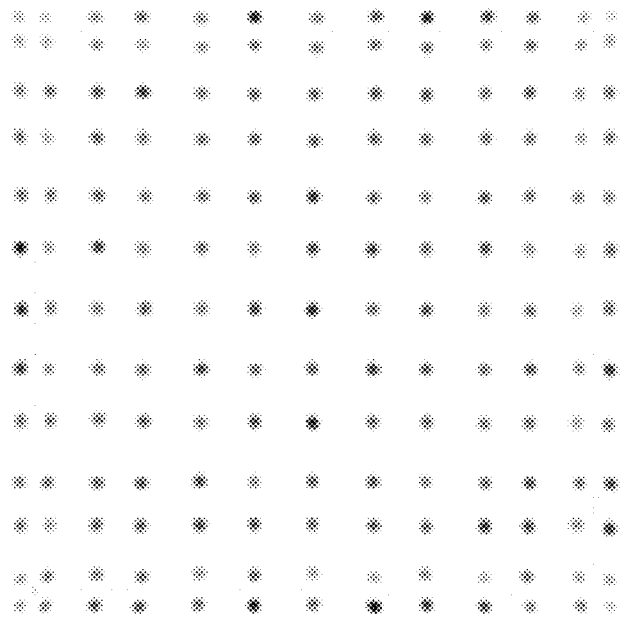
FIG. 3 shows a schematic view of a second position spectrum according to the method for identifying a position spectrum of FIG. 2, wherein one of the second position spectra is obtained after feature extraction on the first position spectrum.

Step S23: calculating determinants of the n Hessian matrices, that is $D = L_{xx} \times L_{yy} - L_{xy}^2$, and generating n second position spectra, as shown in FIG. 3.

In the above-mentioned step S21, a specific value of the second variance may be selected randomly or according to actual experience of the person skilled in the art, which involves no difficulty in the state of art and will not be elaborated herein.

Figure 4:
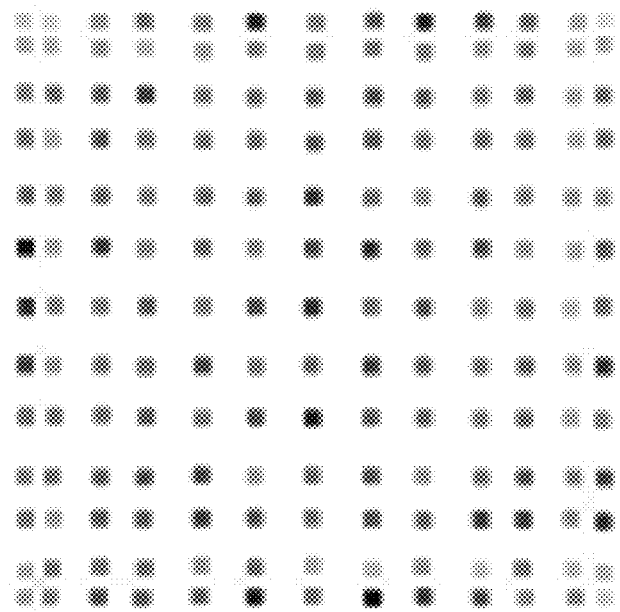
FIG. 4 shows a schematic view of a position spectrum after morphological expansion of the second position spectrum shown in FIG. 2 in the method for identifying a position spectrum according to an embodiment of the present invention.
Figure 5:
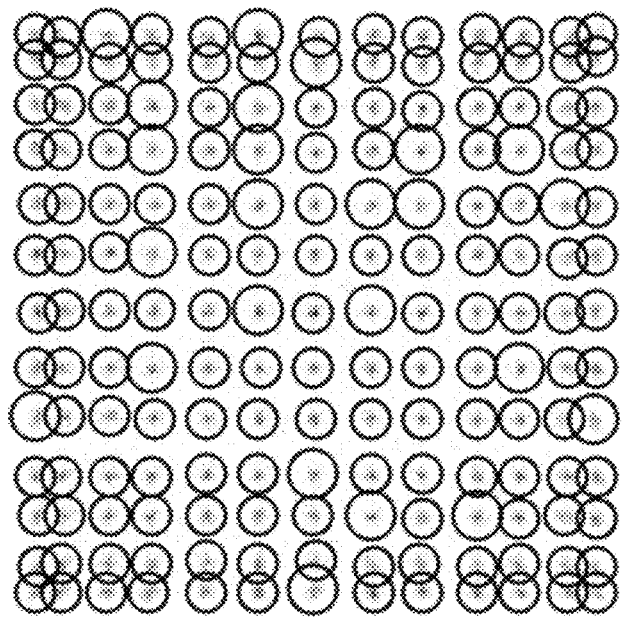
FIG. 5 shows a schematic view of a fourth position spectrum according to the method for identifying a position spectrum of FIG. 4, wherein the third position spectrum is obtained after peak search on the second position spectrum.

In the above-mentioned step S3, before performing the peak search, the n second position spectra may be morphologically expanded to generate n expanded position spectra, as shown in FIG. 4. The peak search is performed to search for N maximum values among the n expanded position spectra, and to obtain the position coordinates and the values of the second variances corresponding to the N values, so as to form the third position spectrum, where N is a number corresponding to that of the scintillation crystals in the PET detector, such that the positions corresponding to the N maximum values are identified as N peak points, the expansion position spectrum of each peak point corresponding to the size of the second Gaussian template variance. Usually, triple the second Gaussian template variances are taken as the radii of the respective crystals in the third position spectrum, as shown in FIG. 5.

Figure 6:
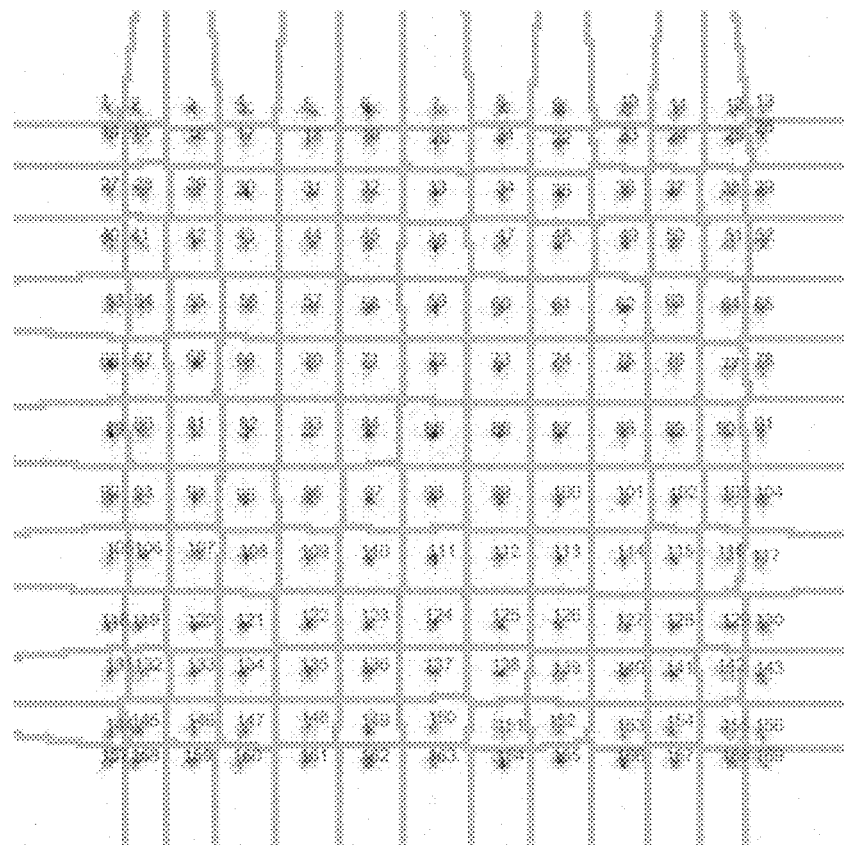
FIG. 6 shows a schematic view of a final position spectrum after segmentation according to an embodiment of the present invention, wherein the initial position spectrum is obtained by a SiPM detector.

For the neatly arranged and clearly distributed position spectra, step S4 may be performed directly after the processing of steps S1-S3. In step S4, globally numbering may be performed by neighborhood ranking of peak points, and the specific steps may include:

step S41: obtaining the position coordinates and position response radii of all the peak points, wherein the position coordinates of the peak points conform to the originally established XOY coordinate system, and the position response radius may be selected according to the actual cross-sectional size of the crystal bar, such as usually taking triple the second Gaussian template variances as the position response radii of the respective peak points;

step S42: extracting the zones Where the position coordinates of the peak points are located within the position response radii, wherein if the number of the peak points is N, then the number of extracted zones is also N;

step S43: calculating the minimum values of the corresponding coordinate in each zone in the row/column direction; specifically, when evaluating in the rows, it is needed to evaluate the smallest y value among all the points in the entire zone; when evaluating in the columns, it is needed to evaluate the smallest x value among all the points in the entire zone;

step S44: ranking the N minimum values, such that the peak points corresponding to the $m \times (n-1)+1^{th}$ to $m \times n^{th}$ minimum values belong to the $n^{th}$ row/column, Where m is the number of crystals in a row/column, n is a natural number; and step S45: numbering the rows/columns assigned according to the peak points in the actual geometric order of the crystal array, and displaying the numbers adjacent to the peak points to form a sixth position spectrum, as shown in FIG. 6, in which the numbers refer to the result of the global numbering.

In the above-mentioned step S5, event clustering refers to after obtaining the position coordinates of the peak points in the position spectrum, clustering all the single events according to the position information to generate a crystal lookup table. Since the annihilation of the positron and the electron produces a pair of photons with the same energy and opposite directions, each detected photon event containing the information of the annihilation position, time, and energy, it is needed to cluster all the single photons, to identify which crystal bar each photon event comes from, and to correspond each photon event to one light spot in the position spectrum, in order to accurately determine the position information. Specifically, event clustering may include the following steps:

step S51: randomly selecting position coordinate of a single event, and calculating distances between the position coordinate and position coordinates of the N identified peak points, where N is the number of crystals;

step S52: selecting the crystal with the shortest distance among the N distances in the step S51 as the crystal cluster of the position coordinates in the step S51; and step S53: traversing the position coordinates of all the single events to obtain crystal clusters for all the position coordinates, and thereby forming a final position spectrum, as shown in FIG. 6.

In addition, in the above-mentioned step S5, the peak point positions of the identified crystals may also be used to initialize the Gaussian function mean in GMM (Gaussian Mixture Model), the initial neuron weights in SOM (Self-Organizing Mapping algorithm), and the center of the clustering in the KNN algorithm (K-Nearest Neighbor algorithm) so as to efficiently obtain single-event crystal clusters. The specific steps will not be elaborated.

In the above-mentioned stir S51, the position coordinates of the single events are essentially the pixel number of the position spectrum. The light spot represents the crystal. For example, for a 13×13 array of crystal bars, the total pixel value is 256×256, which means that there are 256×256 positions for the photons to hit on. Therefore, in a position spectrum with a size of 256×256 pixels, for the single event located in the first row and first column, its location coordinate is (1, 1), and for the single event located in the $i^{th}$ row and $j^{th}$ column, its location coordinate is (i, j).

Figure 7:
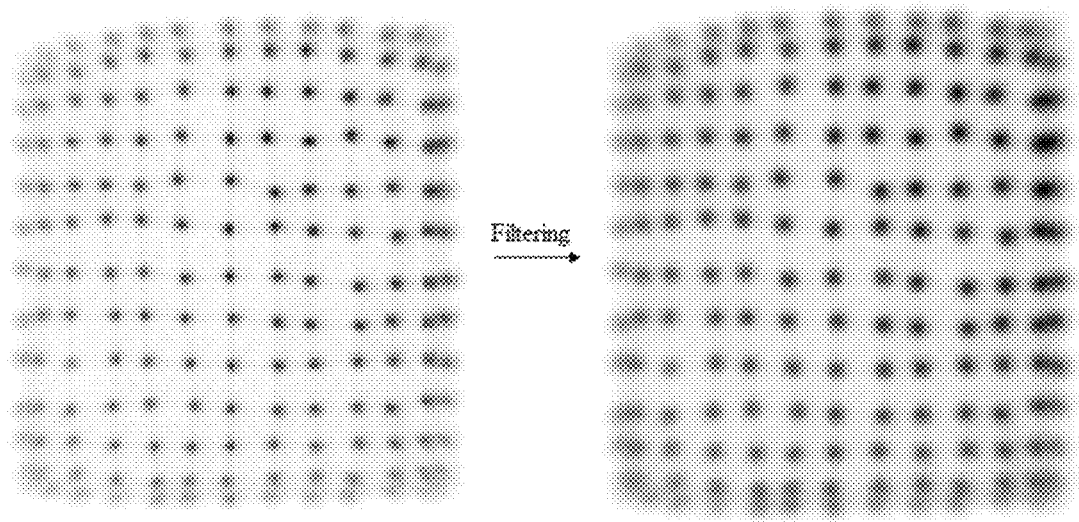
FIG. 7 shows a schematic view of the effect of the method for identifying position spectra according to an embodiment of the invention, in which the initial position spectrum (left) is obtained by a PSPMT (Position Sensitive Photomultiplier Tube) detector, and the first position spectrum (right) can be obtained by means of filtering process of the initial position spectrum.

In the above-mentioned embodiment, step S1 to step S5 may process and identify the position spectrum with higher accuracy, faster speed and higher efficiency, and are especially suitable for the position spectrum that is neatly arranged and clearly distributed, such as the initial position spectrum obtained by the SiPM (silicon photomultiplier) detector, as shown in FIG. 2. However, for the position spectrum which is disarrayed and fuzzily distributed, such as the initial position spectrum acquired by the PSPMT (Position Sensitive Photomultiplier Tube) detector as shown in FIG. 7, after processing in accordance with the above steps S1-S3, there are many erroneous peak points. Therefore, it may be needed to perform removal of invalid values, assignment of rows or columns, and prediction of missing points after the peak search, in order to improve the effect of identifying and predicting the fuzzily distributed crystals.

In a further embodiment, the method for identifying a position spectrum provided in the disclosure may further include the following steps:

step S1: pre-processing an initial position spectrum to generate a first position spectrum;

step S2: extracting features from the first position spectrum to generate a plurality of second position spectra;

step S3: performing a peak search on the second position spectra to obtain N peak points, where N is the number of scintillation crystals in the detector; wherein after the peak search, steps S31 to S33 may be performed;

step S31: removing invalid peak points in the third position spectrum to generate a fourth position spectrum;

step S32: assigning rows or columns of the peak points after the removal to generate a fifth position spectrum;

step S33: predicting missing peak points to generate the third position spectrum;

step S4: globally numbering the peak points in the third position spectrum to form a sixth position spectrum; and step S5: clustering single events based on the peak points in the sixth position spectrum to form a final position spectrum, so as to realize the segmentation of the position spectrum.

Figure 8:
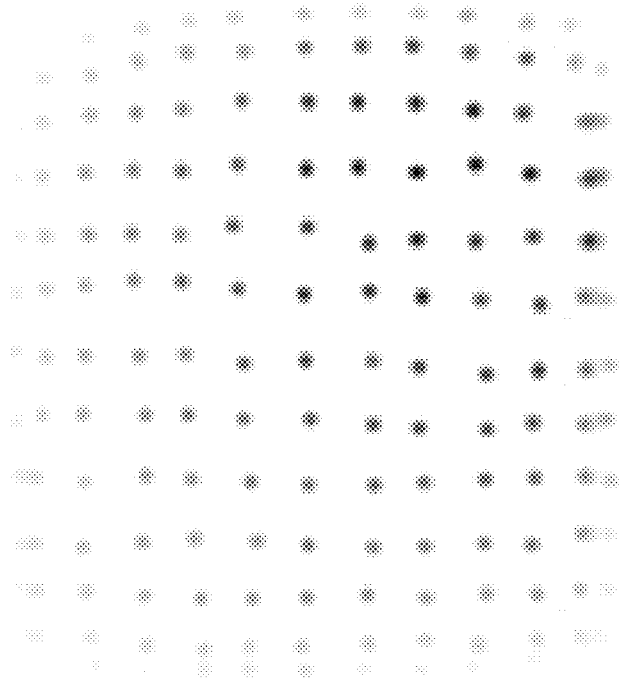
FIG. 8 shows a schematic view of a second position spectrum according to the method for identifying a position spectrum of FIG. 6, wherein one of the second position spectra is obtained after feature extraction on the first position spectrum.
Figure 9:
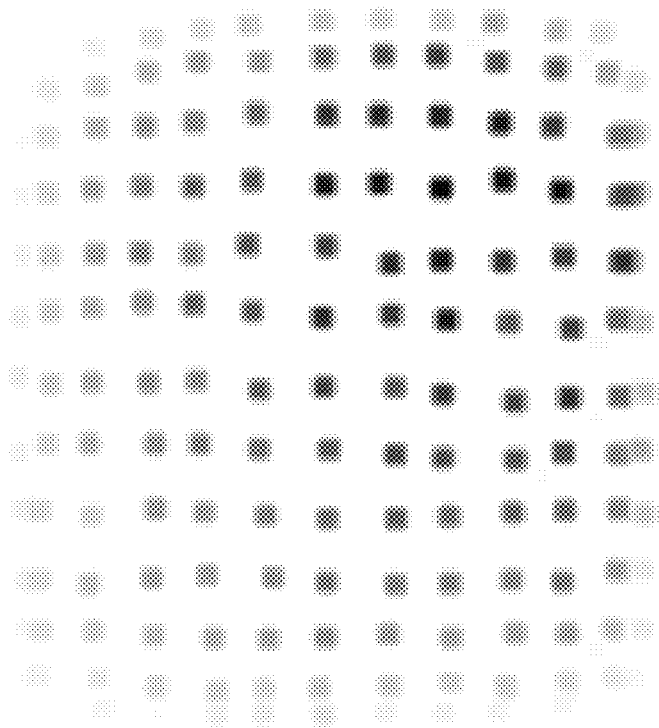
FIG. 9 shows a schematic view of a position spectrum after morphological expansion of the second position spectrum shown in FIG. 7 in the method for identifying a position spectrum according to an embodiment of the present invention.

The specific methods in the above-mentioned step S1 and step S2 are similar or the same as those in the previous embodiments, and will not be elaborated here. For example, the pre-processing effect of the initial position spectrum obtained by the PSPMT (Position Sensitive Photomultiplier Tube) detector which is disarranged with blurred distribution is shown in FIG. 7; the position spectrum after the feature extraction is shown in FIG. 8, and the effects after the morphological expansion and peak search are shown in FIGS. 9 and 10, respectively.

Figure 10:
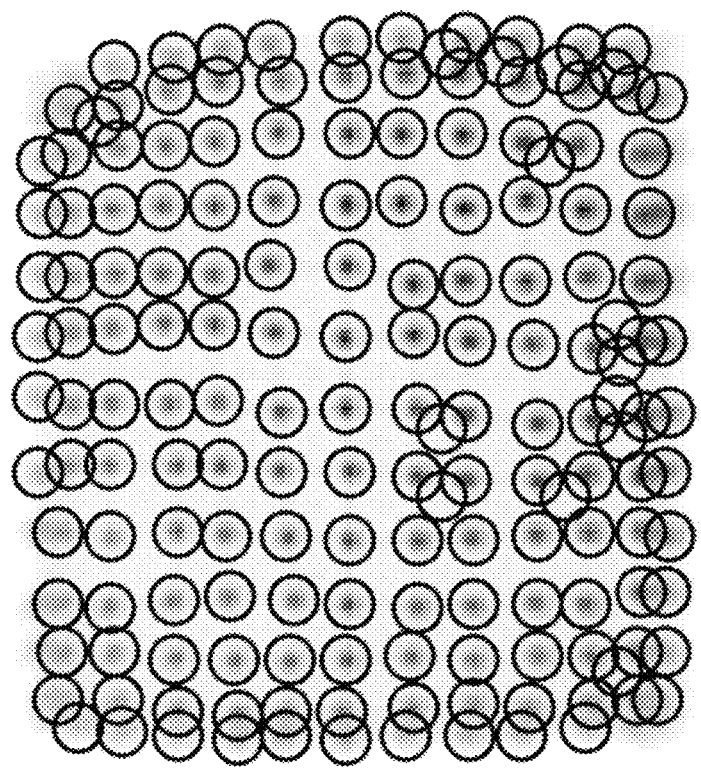
FIG. 10 shows a schematic view of a third position spectrum after peak search of the position spectrum shown in FIG. 8 in the method for identifying a position spectrum according to an embodiment of the present invention.
Figure 11:
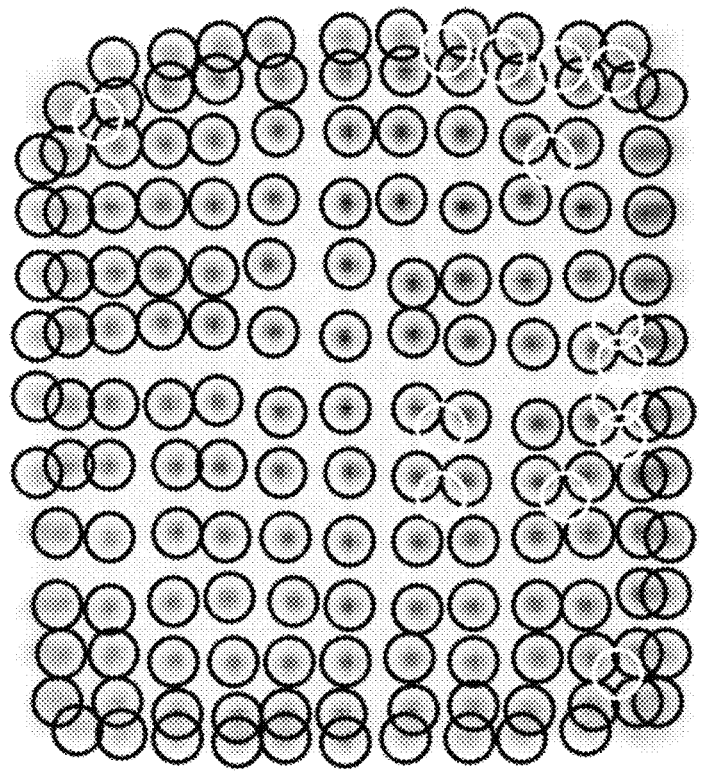
FIG. 11 shows a schematic view of a fourth position spectrum according to the method for identifying a position spectrum in an embodiment of the invention, wherein the fourth position spectrum is obtained after invalid value removal on the third position spectrum, and wherein the white circles mark the erroneously identified peak points which need to be removed.

In the above-mentioned step S31, the specific steps of removing invalid peak points may include:

step S311: extracting the image of zones where the peak points are located according to the position coordinates of the peak points identified by the peak search and the second variances, as shown in FIG. 10;

step S312: determining an initial segmentation threshold T, recording the ratio of the number of pixels smaller than the initial segmentation threshold T in the image of the position distribution zones to the number of all pixels as w0, and the average gray as u0; recording the ratio of the number of pixels greater than the initial segmentation threshold T in the image of the position distribution zones to the number of all pixels as w1; and the average gray level as u1; and recording the average gray level of the image of the overall position distribution zones as u;

step S313: calculating the inter-class variance k according to the formula $k=w_0 \times w_1 \times (u_0-u_1)^2$;

step S314: traversing the values of the initial segmentation threshold T to maximize the inter-class variance k, thereby obtaining a binarized image of the position distribution zones of the crystals;

step S315: obtaining a neighborhood in the center of the binarized image and calculating a pixel sum, wherein if the value of the pixel sum in the neighborhood is 0, the peak point is determined to be an erroneously identified peak point, that is, an invalid peak point; as shown in FIG. 11, the white circles mark the erroneously identified peak points.

In the above-mentioned step S32, the assignment of rows or columns may comprise the specific steps according to the rows or columns of the crystal arrangement. Here, taking the assignment of the rows as an example, the assignment of rows or columns may comprise the specific steps of:

step S321: ranking the position coordinates of the peak points identified in the step S31 according to the corresponding dimensional coordinate;

step S322: if ranking according to the x coordinate, extracting the $m \times (n-1)+1^{th}$ to $m \times n^{th}$ peak points as a fuzzy row set of the $n^{th}$ row, where m is the number of crystals on each row, and n is a Natural number;

step S323: randomly selecting p peak points from the fuzzy row set of the $n^{th}$ row as the point set S participating in the fitting, with a set of the remaining peak points in the set of remaining extreme points as a remainder set R, where p is the number of samples required for fitting a curve;

step S324: performing quadratic-curve fitting on the extreme points in the point set S according to the least square method;

step S325: obtaining an error sum E for all the peak points in the remainder set R with respect to the quadratic curve;

step S326: iteratively performing step S323 to step S325 until within a certain number of iterations, the minimum value of the error sum E or the error sum E is less than a defined minimum tolerance threshold, such that then the fitted quadratic curve is the distribution curve of peak points in the $n^{th}$ row; and step S327: assigning the identified peak points to the distribution curve of each row/column according to the principle of the assignment of rows or columns.

In the above-mentioned steps S323 to S325, the curve fitting based on the least square method may be easily implemented by the person skilled in the art, and will not be elaborated here.

In the above-mentioned step S326, the minimum tolerance threshold for the error sum E may be determined through experiments. It may be easily determined by the person skilled in the art the range of the minimum tolerance threshold through experiments, which will not be elaborated here.

In the above-mentioned step S327, the essence of the principle of assignment of rows or columns is to assign the peak points in the position spectrum to the intersection of the row or column distribution curves. The principle of assignment of rows or columns includes the near assignment principle and the conflict assignment principle.

The principle of near assignment may include: first, the assignment based on the nearest distance between the peak point and the intersection of the distribution curve; and second, each intersection of the distribution curve occupying at most one peak point, and one peak point being assigned only one intersection.

Figure 12:
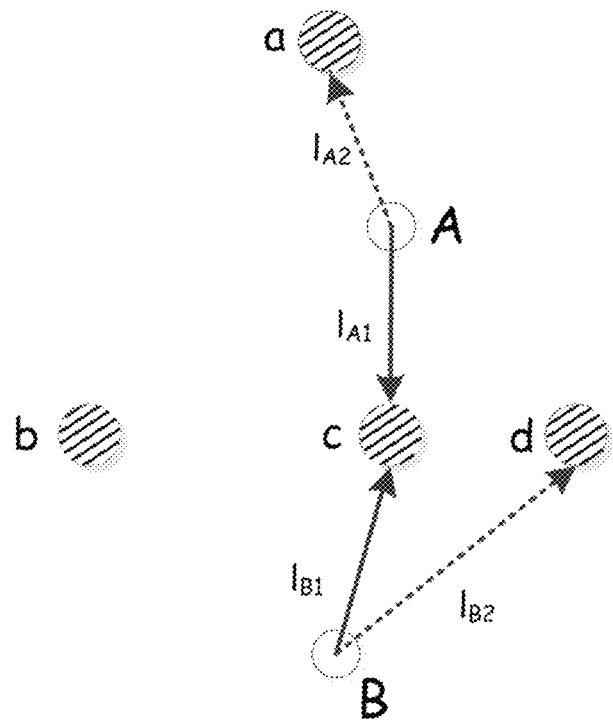
FIG. 12 shows a schematic view of the conflict assignment in the method for identifying a position spectrum according to an embodiment of the invention.
Figure 13:
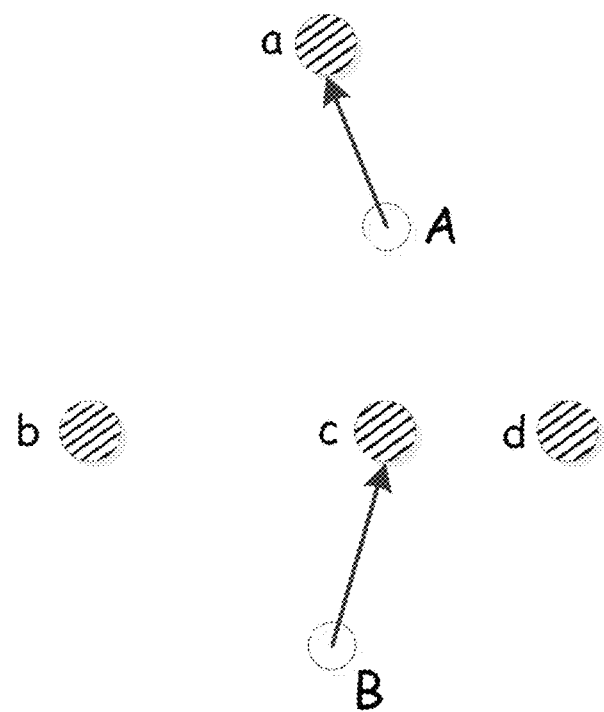
FIG. 13 shows a schematic view of the result after the conflict assignment in the method for identifying a position spectrum as shown in FIG. 11.

Regarding the conflict assignment principle, specifically, for the situation where one intersection corresponds to multiple peak points, as shown in FIG. 12, the hollow circle representing the peak point, and the solid circle representing the intersection of the distribution curve, when the distances from the multiple peak points to the intersection of the distribution curve are the same, the intersection will correspond to the multiple peak points. As shown in FIG. 12, lA1=lB1 means that the intersection c of the distribution curve corresponds to the peak points A and B at the same time, and l represents the distance between the peak point and the intersection of the distribution curve. In the context, the conflict allocation principle may be carried out according to the following steps:

first, finding the corresponding peak points by the intersection of the distribution curve, for example, the two peak points A and B corresponding to the intersection c;

second, finding two nearest intersections for each corresponding peak point; for example, two nearest intersections a and c for the peak point A, and two nearest intersections c and d for the peak point B; and third, comparing the sum of distances between each peak point and the two nearest intersections with each other, the peak point with the greatest sum of distances being assigned to the conflict intersection of the distribution curves; for example, where the distances between the peak point A and the intersection points c and a are lA1 and lA2 respectively, the distances between the peak point B and the intersection points c and d are lB1 and lB2 respectively, the sum of distances between the peak point A and the two closest intersection points c and a being lA1+lA2 which is less than the sum of the distances between peak point B and the two closest intersection points c and d, lB1+lB2, such that the peak point B is assigned to the intersection c, and the peak point A is assigned to a Farther, nearest intersection a, where the distribution result is shown in FIG. 13.

Figure 14:
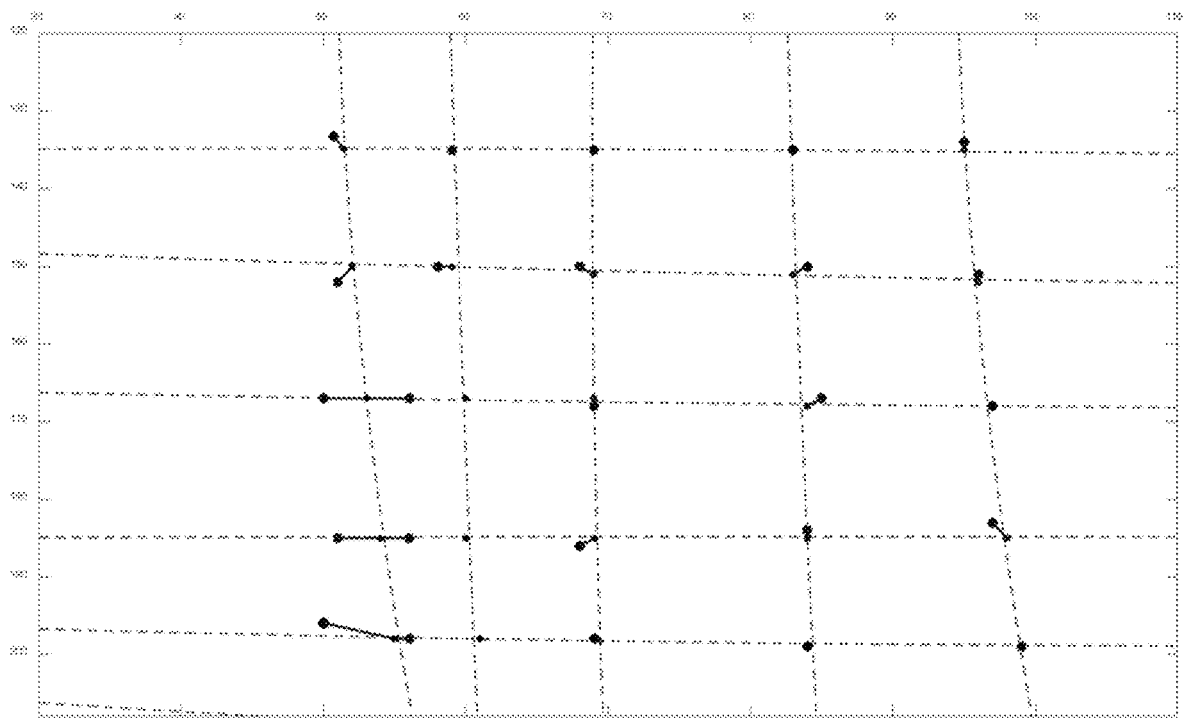
FIG. 14 shows a schematic view of a fifth position spectrum after assignment of rows and columns according to an embodiment of the present invention, wherein the initial position spectrum is obtained by a SiPM detector.
Figure 15:
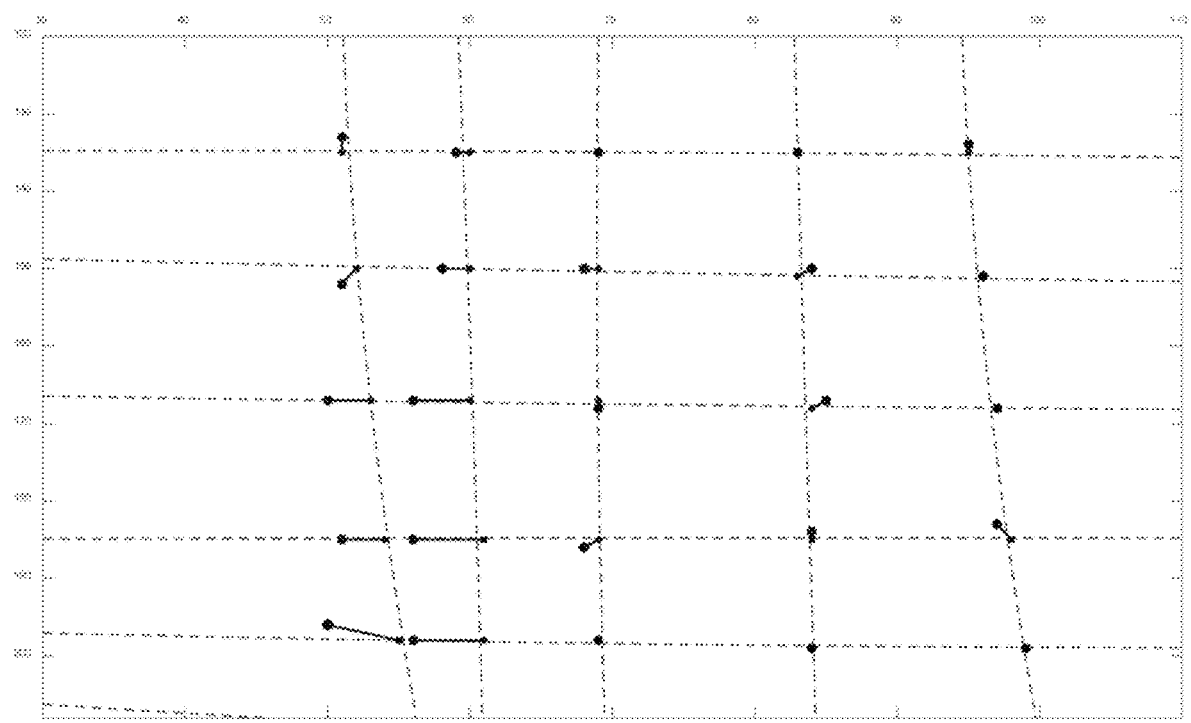
FIG. 15 shows a schematic view of a fifth position spectrum after assignment of rows and columns according to an embodiment of the present invention, wherein the initial position spectrum is obtained by a PSPMT detector.
Figure 16:
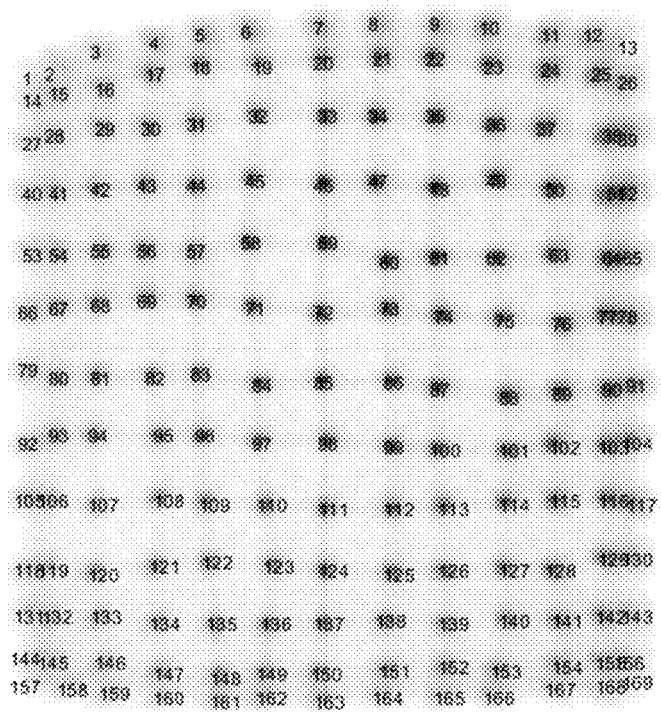
FIG. 16 shows a schematic view of a sixth position spectrum after global numbering in the method for identifying a position spectrum according to an embodiment of the present invention.
Figure 17:
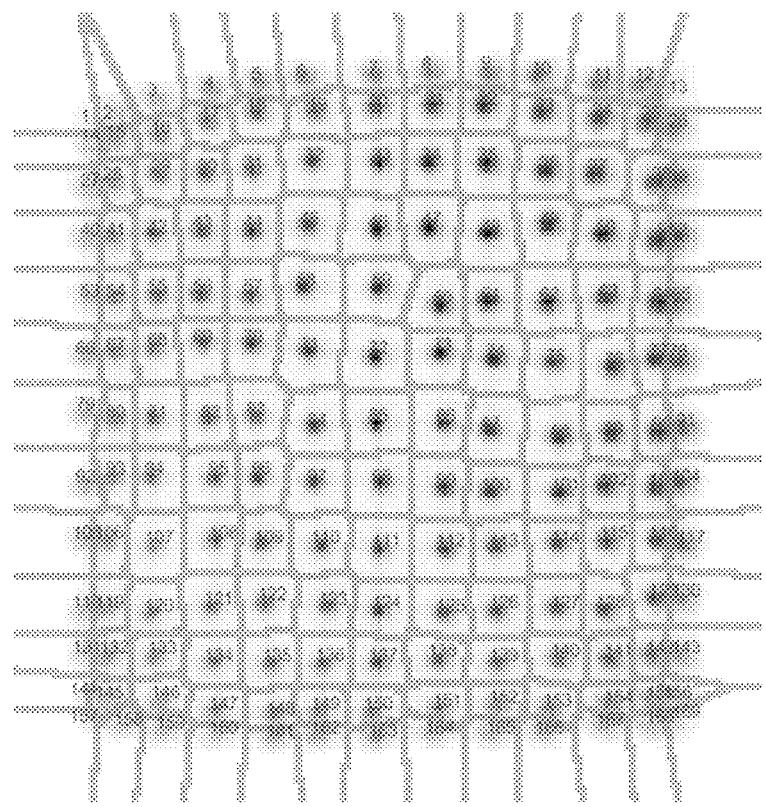
FIG. 17 shows a schematic view of a final position spectrum after segmentation according to an embodiment of the present invention, wherein the initial position spectrum is obtained by a PSPMT detector.

For the initial position spectrum acquired by the PSPMT (Position Sensitive Photomultiplier Tube) detector, the position spectrum after peak search and invalid value removal is shown in FIG. 11; the position spectrum before the assignment of rows or columns is shown in FIG. 14, and it can be seen that some of the peak points share the same intersection of the distribution curve; and the position spectrum after the assignment of rows or columns is shown in FIG. 15, and it can be seen that each and every the peak point after the assignment of rows or columns corresponds to the intersections of the distribution curve in a manner of one-to-one.

Further, since the number of crystals finally identified or the number of peak points is less than the target number after the error identification and removal, it is needed to further predict the position of the missing crystals, that is, performing step S33. In the above-mentioned step S33, the prediction of the missing peak points is performed based on the results of the assignment of rows or columns in the intersections of the distribution curve. After the assignment of rows or columns, each of the identified peak points has only one intersection of the distribution curve corresponding thereto. Prediction of the missing points is to find out the coordinates of the intersection unassigned with peak points, and then the coordinates of the intersection are to be assigned to the missing peak points in the current row and the current column.

Those skilled in the art need to pay attention to that, for the position spectrum which is disarranged and fuzzily distributed, since it may require for the steps of invalid value removal, assignment of rows or columns, and missing point prediction, step S4 may be performed directly according to the result of the assignment of rows or columns, which will not be elaborated here.

Although the method steps described in the above-mentioned embodiments or flowcharts are provided in the disclosure, more or fewer steps may be included in the method with conventional or routine work. Steps, in which there is no necessary causal relationship logically, may be executed in a sequence other than those provided in the embodiments in the disclosure.

By means of the position spectrum segmentation method provided in the disclosure, any position spectrum may be processed as needed or the position spectrum may be segmented before being processed as needed. For example, for the position spectrum with blurred edges and severe distortion, it may directly follow the steps S1-S2-S3-S31, S32, S33-S4-S5 for segmentation, or for the neatly arranged and clearly distributed position spectrum, it may follow the steps S1-S2-S3-S4-S5 for segmentation. In a word, the method provided in the disclosure may realize the identification of the position spectrum of fuzzy edges and severe distortion in high efficiency and high accuracy, meanwhile, it may support the effective identification of the position spectrum generated by various structural detectors.

Figure 18:
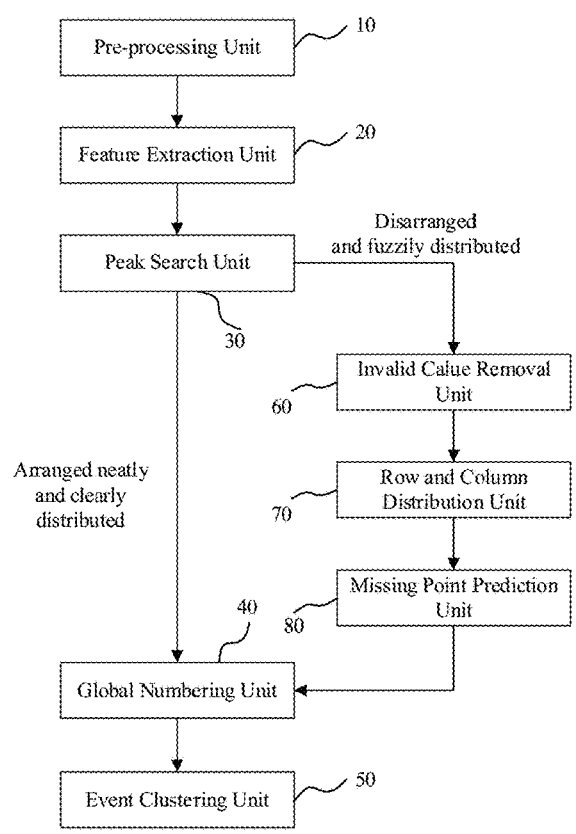
FIG. 18 shows a schematically structural diagram of a device for identifying a position spectrum according to an embodiment of the present invention.

Further, as shown in FIG. 18, in the disclosure, a device for identifying a position spectrum, which may be based on the above-mentioned method, is provided. The device includes a pre-processing unit 10, a feature extraction unit 20, a peak search unit 30, a global numbering unit 40, and an event clustering unit 50. The preprocessing unit 10 is configured to receive an initial position spectrum output from the detector and pre-process the initial position spectrum to form a first position spectrum. The feature extraction unit 20 is configured to receive the first position spectrum and extract features from the first position spectrum to generate second position spectra. The peak search unit 30 is configured to receive the second position spectra and perform a peak search on the second position spectra to form a third position spectrum. The global numbering unit 40 is configured to globally number the peak points in the third position spectrum to form a sixth position spectrum. The event clustering unit 50 is configured to cluster single events based on the peak points in the sixth position spectrum to form a final position spectrum, so as to realize the segmentation of the position spectrum.

The initial position spectrum may be obtained by apparatus or method commonly used in the art, e.g., by a SiPM detector and by means of a multi-threshold sampling method, or by a PSPMT detector and by means of a traditional time interval sampling method.

Specifically, the pre-processing unit 10 may use two-dimensional Gaussian filtering to pre-process the initial position spectrum. The pre-processing unit 10 may define a size and a first variance of the first Gaussian template randomly or according to actual experience of the person skilled in the art, and then perform convolutional processing of the initial position spectrum with the first Gaussian template to generate the first position spectrum. By means of pre-processing, each light spot in the initial position spectrum may become more uniform and obvious. That is, the shape and distribution of the light spots in the initial position spectrum become closer to a two-dimensional Gaussian function, as shown in FIG. 2.

Further, it is needed to perform feature extraction on the light spots in the first position spectrum for the capacity of correctly identifying the light spot in a wider range. Therefore, the feature extraction module 20 may evaluate the similarity between the light spots and a differential operator in terms of the distribution features of the light spots by means of a derivative-based differential method. The distribution features of the light spots refer to the distribution of the light spots on the two-dimensional coordinate, such as the arrangement and shape of the light spots, which may include high middle counts in the middle and low counts in the periphery, that is, the middle of the light spots is clear and the periphery of the light spots is blurred. The feature extraction module 20 may perform feature extraction according to the following specific steps:

step S21: pre-defining a set of second variances $\sigma_1$, $\sigma_2$, . . . , $\sigma_n$ where n is a natural number, and $\sigma_n$ generating a two-dimensional Gaussian template according to each second variance with the same size, that is, generating n second Gaussian templates, denoted as g;

Step S22: finding a solution of a convolution of each second Gaussian template and the first position spectrum, that is, finding the Hessian matrices:

first, calculating a second-order partial derivative of the second Gaussian template with respect to x according to the various second variances:

$$\frac{\partial^2 g}{\partial x^2} = \frac{1}{2\pi\sigma^4} e^{-\frac{x^2+y^2}{2\sigma^2}} \left(\frac{x^2}{\sigma^2} - 1\right);$$

second, calculating a second-order partial derivative of the second Gaussian template with respect to y according to the various second variances:

$$\frac{\partial^2 g}{\partial y^2} = \frac{1}{2\pi\sigma^4} e^{-\frac{x^2+y^2}{2\sigma^2}} \left(\frac{y^2}{\sigma^2} - 1\right);$$

third, calculating a partial derivative with respect to y based on a partial derivative of the second Gaussian template with respect to x according to different second variances:

$$\frac{\partial^2 g}{\partial x \partial y} = \frac{1}{2\pi\sigma^4} e^{-\frac{x^2+y^2}{2\sigma^2}} \left(\frac{xy}{\sigma^2}\right);$$

finally, normalizing the said three partial derivatives, that is, multiplying $\sigma^2$, and then convolving the three partial derivatives with the first position spectrum respectively to obtain n $L_{xx}$, $L_{xy}$, $L_{yy}$, such that n Hessian matrices may be obtained, namely $$H(L) = \begin{bmatrix} L_{xx} & L_{xy} \\ L_{xy} & L_{yy} \end{bmatrix};$$

Step S23: calculating determinants of the n Hessian matrices, that is $D=L_{xx} \times L_{yy} - L_{xy}^2$, and generating n second position spectra, as shown in FIG. 3.

The peak search unit 30 may be configured to perform morphological expansion operations on the n second position spectra to obtain n expanded position spectra, and then the peak search unit 30 is configured to search for N maximum values among the expanded position spectra, so as to form the third position spectrum, wherein N is the number of the corresponding scintillation crystals in the PET detector.

For a neatly arranged and clearly distributed position spectrum, after being processed by the preprocessing unit 10, the feature extraction unit 20, and the peak search unit 30, the global numbering module 40 may be used for global numbering, which may be performed in a manner of neighborhood ranking of peak points, comprising the specific steps of:

step S41: obtaining the position coordinates and position response radii of all the peak points, wherein the position coordinates of the peak points conform to the originally established XOY coordinate system, and the position response radius may be selected according to the actual cross-sectional size of the crystal bar, such as usually taking triple the second Gaussian template variances as the position response radii of the respective peak points;

step S42: extracting the zones where the position coordinates of the peak points are located within the position response radii, wherein if the number of the peak points is N, then the number of extracted zones is also N;

step S43: calculating the minimum values of the corresponding coordinate in each zone in the row/column direction; specifically, when evaluating in the rows, it is needed to evaluate the smallest y value among all the points in the entire zone; when evaluating in the columns, it is needed to evaluate the smallest x value among all the points in the entire zone;

step S44: ranking the N minimum values, such that the peak points corresponding to the m×(n−1)+1$^{th}$ to m×n$^{th}$ minimum values belong to the n$^{th}$ row/column, where m is the number of crystals in a row/column, n is a natural number; and step S45: numbering the rows/columns assigned according to the peak points in the actual geometric order of the crystal array, and displaying the numbers adjacent to the peak points to form a sixth position spectrum, as shown in FIG. 6, in which the numbers refer to the result of the global numbering.

Finally, the event clustering unit 50 is configured to cluster all the single events according to the position information to generate a crystal lookup table. The event clustering unit 50 may be configured to perform the following steps:

step S51: randomly selecting position coordinate of a single event, and calculating distances between the position coordinate and position coordinates of the N identified peak points, where N is the number of crystals;

step S52: selecting the crystal with the shortest distance among the N distances in the step S51 as the crystal cluster of the position coordinates in the step S51; and step S53: traversing the position coordinates of all the single events to obtain crystal clusters for all the position coordinates, and thereby forming a final position spectrum, as shown in FIG. 6.

However, for the position spectrum which is disarrayed and fuzzily distributed, such as the initial position spectrum acquired by the PSPMT (Position Sensitive Photomultiplier Tube) detector as shown in FIG. 7, after being processed the pre-processing unit 10, the feature extraction unit 20, the peak search unit 30, there are many erroneous peak points. Therefore, it may be needed to be processed by an invalid value removal unit 60, a row and column assignment unit 70, and a missing point prediction unit 80 after being processed by the peak search unit 30, in order to improve the effect of identifying and predicting the fuzzily distributed crystals. The processing of the invalid value removal unit 60, the row and column assignment unit 70, and the missing point prediction unit 80 may conform to the step of removing invalid value, the step of assignment of rows or column, and the step of predicting missing points in the second embodiment described above, and will not be elaborated here. The invalid value removal unit 60 is configured to perform adaptive error filtering based on the features of the erroneous identification zones, is able to solve the problem that extracting features from the position spectrum with fuzzy distribution will get erroneous peak points, and may effectively remove most of the erroneous peak point positions. The row and column assignment unit 70 may be configured such that each of the identified peak points has only one intersection of the distribution curve corresponding thereto. The missing point prediction unit 80 may find out the coordinates of the intersection unassigned with peak points, and then assign the coordinates of the intersection to the missing peak points in the current row and the current column.

By means of the position spectrum segmentation device provided in the disclosure, any position spectrum may be processed as needed or the position spectrum may be segmented before being processed as needed. For example, for the neatly arranged and clearly distributed position spectrum, it may directly be segmented by the pre-processing unit, the feature extraction unit, the peak search unit, the global numbering unit, and the event clustering unit; or for the position spectrum with blurred edges and severe distortion, it may be further processed by the invalid value removal unit, the row and column assignment unit, and the missing point prediction unit for segmentation. In a word, the device provided in the disclosure may realize the identification of the position spectrum of fuzzy edges and severe distortion in high efficiency and high accuracy, meanwhile, it may support the effective identification of the position spectrum generated by various structural detectors.

In the disclosure, a computer storage medium is also provided which stores a computer program, wherein when the computer program is executed by a processor, the steps of the method in the above-mentioned embodiments may be realized, such as: pre-processing an initial position spectrum to generate a first position spectrum; extracting feature from the first position spectrum to generate a plurality of second position spectra; performing a peak search on the second position spectra to obtain N peak points, which form a third position spectrum, wherein N is the number of scintillation crystals in a detector; globally numbering the peak points in the third position spectrum to form a sixth position spectrum; and clustering single events based on the peak points in the sixth position spectrum to form a final position spectrum, so as to realize the segmentation of the position spectrum. In addition, when the computer program is executed, it may be realized that the invalid peak points in the third position spectrum are removed to obtain the fourth position spectrum, and all the peak points after the removal are assigned to form the fifth position spectrum.

For the detailed description of this embodiment, reference may be made to the detailed description of the method for segmentation of the position spectrum in the foregoing embodiment, which will not be repeated here.

The computer storage medium in the disclosure may include any entity or device capable of storing computer program code, such as ROM/RAM, magnetic disk, optical disk, flash memory or other memories, which will not be listed here.

The devices, units or the like described in the above embodiments may be specifically implemented by computer chips and/or components or implemented by products with specific functions. For the convenient purpose, description is made respectively of different functional units of the devices. Of course, when implementing the embodiments of the invention, the functions of the individual units may be embodied in the same or various computer chips.

What has been described above is only preferred embodiments of the invention and is not intended to limit the scope of the invention. Various alternatives may be made to the said embodiments of the invention. In this regard, any simple or equivalent change or modification made according to the claims and the description falls within the scope of the invention as prescribed in the claims. What is not described in details in the disclosure is conventional.

What is claimed is:

1. A method for identifying a position spectrum, the position spectrum being a two-dimensional position distribution image of photons, and containing position information of all photons extracted from single events output from a detector, wherein the method comprises the following steps:
   step S1: pre-processing an initial position spectrum to generate a first position spectrum;
   step S2: extracting features from the first position spectrum to generate a plurality of second position spectra;
   step S3: performing a peak search on the second position spectra to obtain N peak points, which form a third position spectrum, wherein N is the number of scintillation crystals in the detector, comprising:
      step S31: removing invalid peak points in the third position spectrum to form a fourth position spectrum;
      step S32: assigning rows or columns of all the peak points after the removal to form a fifth position spectrum;
      step S33: predicting missing peak points in the fifth position spectrum to form the third position spectrum;
   step S4: globally numbering the peak points in the third position spectrum to form a sixth position spectrum; and
   step S5: clustering the single events based on the peak points in the sixth position spectrum to form a final position spectrum, so as to realize the position spectrum segmentation.

2. The method for identifying the position spectrum according to claim 1, wherein in the step S1, the pre-processing comprises specific steps of: selecting a size and a first variance of a first Gaussian template, and processing the initial position spectrum by means of convolution with the first Gaussian template to generate the first position spectrum.

3. The method for identifying the position spectrum according to claim 1, wherein in the step S1, the feature extraction comprises specific steps of:
   step S21: determining a set of second variances $\sigma_1, \sigma_2, \ldots, \sigma_n \sigma_n$, where n is a natural number, and generating n Gaussian templates according to each of the second variances with the same size, denoted as g;
   step S22: finding Hessian matrices $$H(L) = \begin{bmatrix} L_{xx} & L_{xy} \\ L_{xy} & L_{yy} \end{bmatrix}$$

by a convolution of each second Gaussian template and the first position spectrum,
   wherein, x and y represent the corresponding orthogonal coordinate axes in the image of the position spectrum;
   step S23: calculating determinants of the n Hessian matrices, that is $D = L_{xx} \times L_{yy} - L_{xy}^2$, and generating n second position spectra.

4. The method for identifying the position spectrum according to claim 3, wherein in the step S22, finding the Hessian matrices comprises specific steps of:
   first, calculating a second-order partial derivative of the second Gaussian template with respect to x according to the various second variances:

$$\frac{\partial^2 g}{\partial x^2} = \frac{1}{2\pi\sigma^4} e^{-\frac{x^2+y^2}{2\sigma^2}} \left( \frac{x^2}{\sigma^2} - 1 \right);$$

second, calculating a second-order partial derivative of the second Gaussian template with respect to y according to the various second variances:

$$\frac{\partial^2 g}{\partial y^2} = \frac{1}{2\pi\sigma^4} e^{-\frac{x^2+y^2}{2\sigma^2}} \left( \frac{y^2}{\sigma^2} - 1 \right);$$

third, calculating a partial derivative with respect to y based on a partial derivative of the second Gaussian template with respect to x according to different second variances:

$$\frac{\partial^2 g}{\partial x \partial y} = \frac{1}{2\pi\sigma^4} e^{-\frac{x^2+y^2}{2\sigma^2}} \left(\frac{xy}{\sigma^2}\right);$$

fourth, normalizing the said three partial derivatives, that is, multiplying $\sigma^2$, and then convolving the three partial derivatives with the first position spectrum respectively to obtain n $L_{xx}$, $L_{xy}$, $L_{yy}$, such that n Hessian matrices are obtained.

5. The method for identifying the position spectrum according to claim 1, wherein in the step S3, before performing the peak search, the second position spectra are morphologically expanded to generate expanded position spectra.

6. The method for identifying the position spectrum according to claim 5, wherein in the step S3, the peak search comprises the step of searching for N maximum values among the expanded position spectra, so as to form the third position spectrum.

7. The method for identifying the position spectrum according to claim 1, wherein in the step S4, the globally numbering comprises specific steps of:
    step S41: obtaining the position coordinates and position response radii of all the peak points;
    step S42: extracting the zones where the position coordinates of the peak points are located within the position response radii;
    step S43: calculating the minimum values of a correspondingly dimensional coordinate in each of the zones in the row or column direction;
    step S44: ranking the N minimum values, such that the peak points corresponding to the $m \times (n-1)+1^{th}$ to $m \times n^{th}$ minimum values belong to the $n^{th}$ row/column, where m is the number of scintillation crystals in a row/column, n is a natural number; and
    step S45: numbering the rows or columns assigned according to the peak points in the actual geometric order of the scintillation crystal array, and displaying the numbers adjacent to the peak points to form a sixth position spectrum.

8. The method for identifying the position spectrum according to claim 7, wherein in the step S5, event clustering comprises after obtaining the position coordinates of the peak points in the position spectrum, clustering all the single events according to the position information to generate a crystal lookup table and to obtain the segmentation result of the position spectrum.

9. The method for identifying the position spectrum according to claim 8, wherein the event clustering comprises specific steps of:
    step S51: randomly selecting position coordinate of a single event, and calculating distances between the position coordinate and position coordinates of the N identified peak points;
    step S52: selecting the peak point with the shortest distance among the N distances in the step S51 as the crystal cluster of the position coordinates in the step S51; and
    step S53: traversing the position coordinates of all the single events to obtain crystal clusters for all the position coordinates, and distinguishing different classes from each other to form the final position spectrum.

10. The method for identifying the position spectrum according to claim 1, wherein in the step S31, removing invalid peak points includes the specific steps of:
    step S311: extracting the image of position distribution zones for all the peak points according to the position coordinates of the peak points and the second variances;
    step S312: determining an initial segmentation threshold T, recording the ratio of the number of pixels smaller than a initial segmentation threshold T in the image of the position distribution zones to the number of all pixels as w0, and the average gray as u0; and recording the ratio of the number of pixels greater than the initial segmentation threshold T in the image of the position distribution zones to the number of all pixels as w1, and the average gray level as u1;
    step S313: calculating the inter-class variance k according to the formula $k = w_0 \times w_1 \times (u_0 - u_1)^2$;
    step S314: traversing the values of the initial segmentation threshold T to maximize the inter-class variance k, thereby obtaining a binarized image of the position distribution zones of the single events generated in the scintillation crystals; and
    step S315: obtaining a neighborhood in the center of the binarized image and calculating a pixel sum, wherein if the value of the pixel sum in the neighborhood is 0, the peak point is determined to be an invalid peak point.

11. The method for identifying the position spectrum according to claim 1, wherein in the step S32, the assignment of rows or columns comprises specific steps of:
    step S321: ranking the position coordinates of the peak points identified in the step S31 according to the corresponding dimensional coordinate;
    step S322: extracting the $m \times (n-1)+1^{th}$ to $m \times n^{th}$ peak points as a fuzzy row set of the $n^{th}$ row or column, where m is the number of crystals on each row, and n is a Natural number;
    step S323: randomly selecting p peak points from the fuzzy row set of the $n^{th}$ row or column as the point set S participating in the fitting, with a set of the remaining peak points in the set of remaining extreme points as a remainder set R, where p is the number of samples required for fitting a curve;
    step S324: performing quadratic-curve fitting on the extreme points in the point set S;
    step S325: obtaining an error sum E for all the peak points in the remainder set R with respect to the quadratic curve;
    step S326: iteratively performing step S323 to step S325 until within a certain number of iterations, the minimum value of the error sum E or the error sum E is less than a defined minimum tolerance threshold, to obtain the distribution curve of peak points in the $n^{th}$ row or column; and
    step S327: assigning the identified peak points to the distribution curve of each row/column according to the principle of the assignment of rows or columns.

12. The method for identifying the position spectrum according to claim 1, wherein the principle of assignment of rows or columns includes near assignment principle and conflict assignment principle.

13. The method for identifying the position spectrum according to claim 12, wherein the near assignment principle may include the assignment based on the nearest distance between the peak point and the intersection of the distribution curve, with each intersection of the distribution curve occupying at most one peak point, and one peak point being assigned only one intersection.

14. The method for identifying the position spectrum according to claim 12, wherein the conflict assignment principle comprises: finding the corresponding peak points by the intersection of the distribution curve; finding two nearest intersections for each of the corresponding peak points; and comparing the sum of distances between each peak point and the two nearest intersections with each other, the peak point with the greatest sum of distances being assigned to the conflict intersection of the distribution curves.

15. The method for identifying the position spectrum according to claim 14, wherein in the step S33, predicting the missing points comprises specific steps of: finding out the coordinates of the intersection unassigned with peak points, and assigning the coordinates of the intersection to the missing peak points in the current row and the current column.

16. A computer storage medium, wherein the computer storage medium stores a computer program, wherein when the computer program is executed, the steps of the method according to claim 1 are realized.

17. A device for identifying position spectrum, wherein the device comprises:
- a pre-processing unit configured to receive an initial position spectrum output from a detector and pre-process the initial position spectrum to form a first position spectrum;
- a feature extraction unit configured to receive the first position spectrum and extract features from the first position spectrum to generate second position spectra;
- a peak search unit configured to receive the second position spectra and perform a peak search on the second position spectra to form a third position spectrum;
- a global numbering unit configured to globally number the peak points in the third position spectrum to form a sixth position spectrum;
- an event clustering unit configured to cluster single events based on the peak points in the sixth position spectrum to form a final position spectrum, so as to realize the segmentation of the position spectrum;
- an invalid value removal unit configured to remove invalid peak points in the third position spectrum to form a fourth position spectrum;
- a row and column assignment unit configured to assign rows or columns of the peak points in the fourth position spectrum to form a fifth position spectrum; and
- a missing point prediction unit configured to predict missing peak points in the fifth position spectrum.

* * * * *